(12) United States Patent
Caldwell

(10) Patent No.: US 6,604,409 B1
(45) Date of Patent: Aug. 12, 2003

(54) CIGAR MOISTURE METER

(76) Inventor: Rudolph C. Caldwell, 2212 12th Ave., Rockford, IL (US) 61104

( * ) Notice: Subject to any disclaimer, the term of this patent is extended or adjusted under 35 U.S.C. 154(b) by 0 days.

(21) Appl. No.: 10/016,359

(22) Filed: Oct. 30, 2001

(51) Int. Cl.[7] .......................... G01N 5/02; G01N 25/56
(52) U.S. Cl. ................................................. 73/73; 73/74
(58) Field of Search ...................... 73/73, 77, 74; 340/602

(56) References Cited

U.S. PATENT DOCUMENTS

| | | | | |
|---|---|---|---|---|
| 3,944,916 A | * | 3/1976 | Tillander | 324/65 P |
| 4,020,417 A | * | 4/1977 | Brehob et al. | 324/65 R |
| 4,522,214 A | * | 6/1985 | Osmalov | 131/79 |
| 4,931,775 A | * | 6/1990 | Sheriff | 340/604 |

* cited by examiner

*Primary Examiner*—Helen Kwok
*Assistant Examiner*—Rodney Frank
(74) *Attorney, Agent, or Firm*—Kajane McManus

(57) ABSTRACT

The cigar moisture meter comprises a probe engaged to an ohmmeter circuit, the probe being injected into the tip of a cigar to provide a reading of moisture content within the cigar by a measurement of resistance across the leads of the probe.

15 Claims, 2 Drawing Sheets

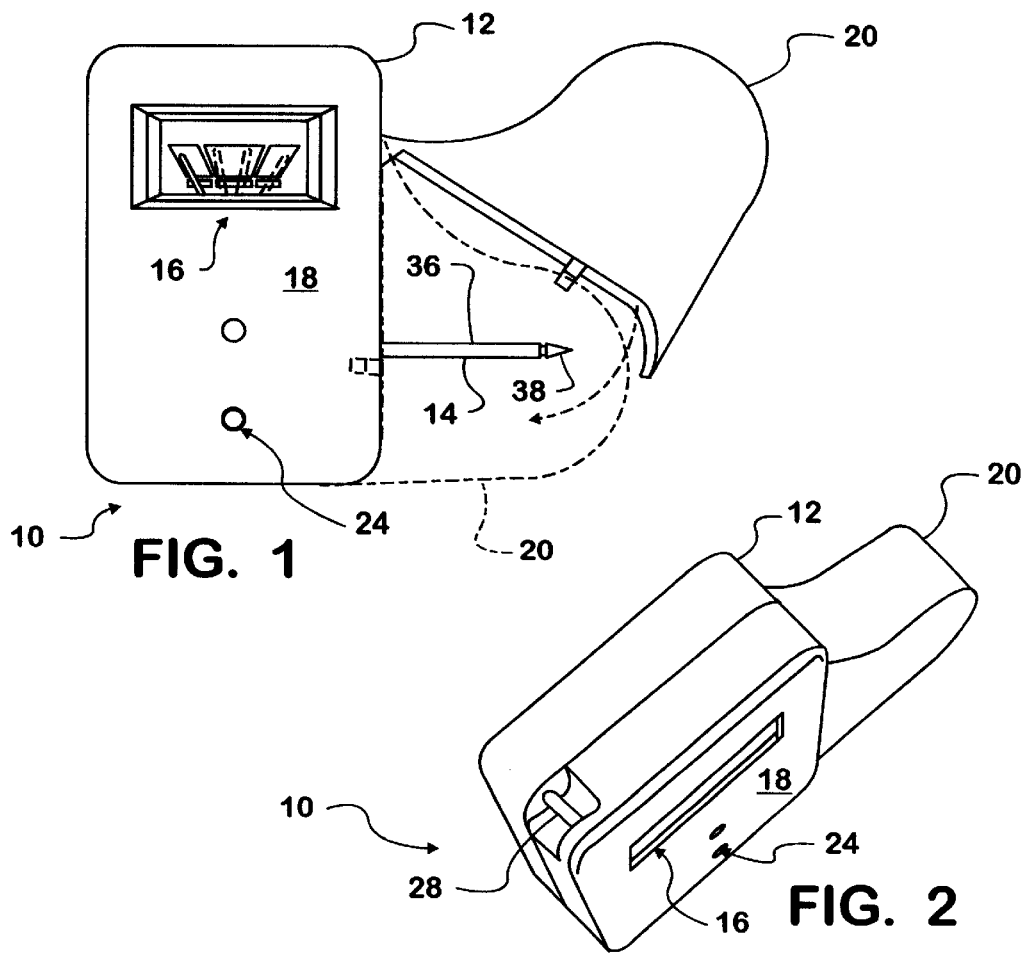
FIG. 1
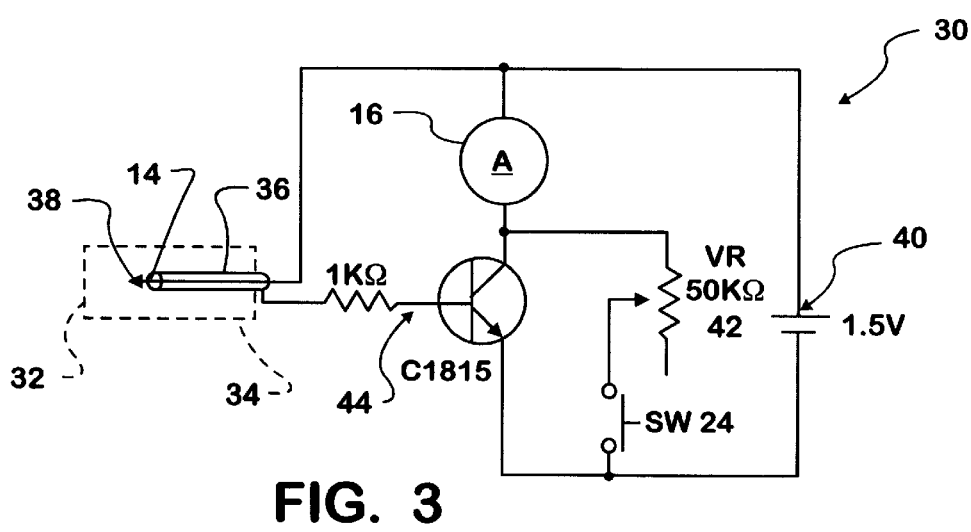
FIG. 2
FIG. 3

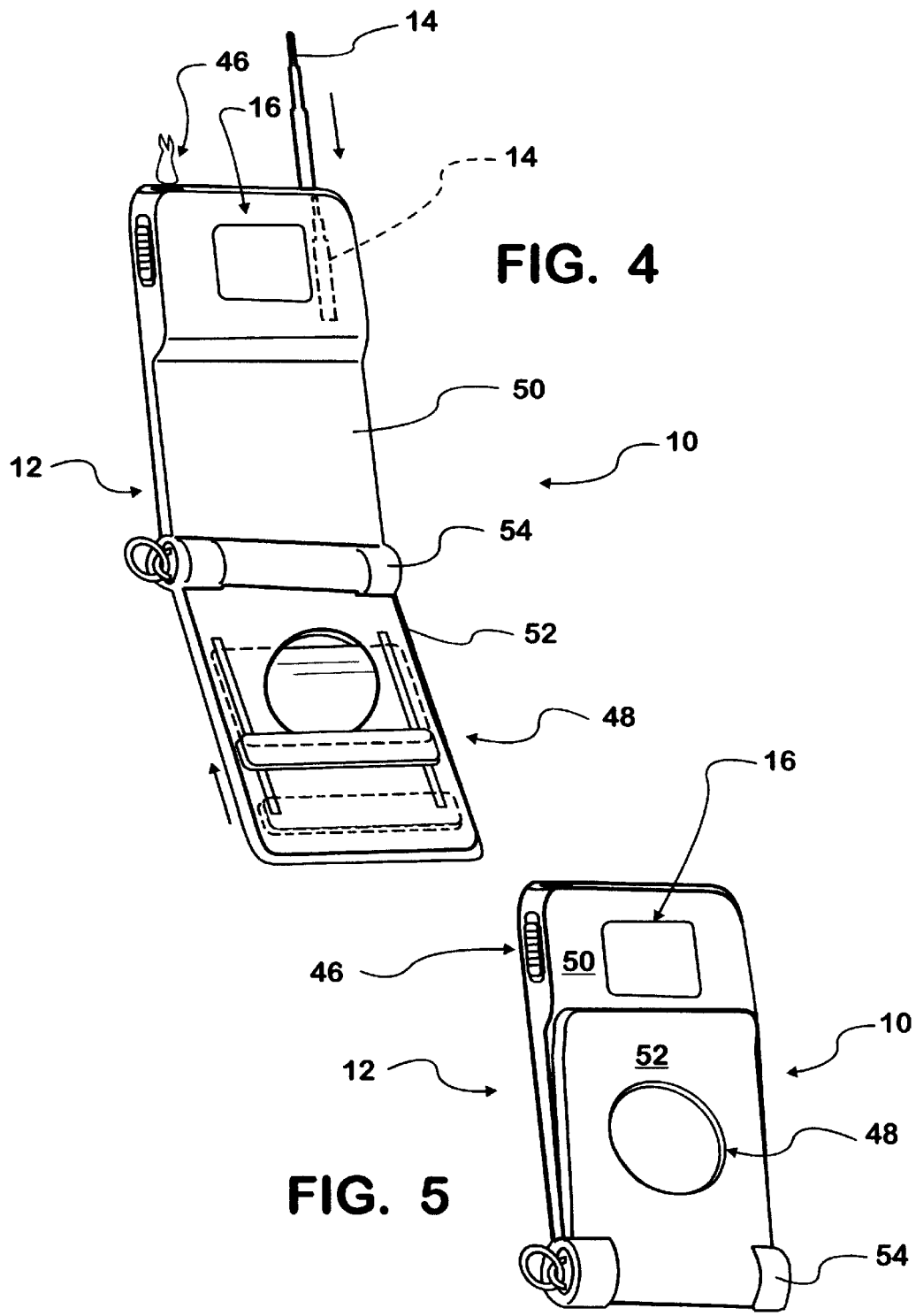

CIGAR MOISTURE METER

BACKGROUND OF THE INVENTION

1. Field of the Invention

The present invention relates to a moisture meter for determining the moisture content of a cigar. More particularly, the moisture meter has a probe insertable into a cigar and engaged to an indicator to advise a smoker if the moisture content of the cigar is suitable for smoking of same.

2. Prior Art

Heretofore various moisture testing apparatus have been proposed for use in the tobacco industry to determine the moisture content of tobacco during processing into cigarettes, cigars, etc.

However, no meter has been available to the cigar aficionado for determining if the moisture content of a cigar is suitable for smoking of same.

SUMMARY OF THE INVENTION

According to the invention there is provided a cigar moisture meter comprising a probe having positive and ground leads of an ohmmeter circuit therein, the probe being injectable into a cigar tip for measuring differential across the leads correlating to a moisture content of the cigar which is indicated on an indicator.

BRIEF DESCRIPTION OF THE DRAWINGS

FIG. 1 is a perspective view of a hand held cigar moisture meter of the present invention.

FIG. 2 is a perspective view of a smaller unit adapted for engagement to a key chain or the like.

FIG. 3 is a circuit diagram of the moisture meter.

FIGS. 4 and 5 provide perspective view of an enhanced embodiment of the hand held cigar moisture meter of the present invention.

DESCRIPTION OF THE PREFERRED EMBODIMENTS

Referring now to the drawings in greater detail, there is illustrated in FIGS. 1 and 2 a cigar moisture meter 10 made in accordance with the teachings of the present invention.

As shown, the meter 10 includes a casing 12 from which a probe 14 protrudes. The probe 14 is electronically engaged to an indicator 16 visible in a front wall 18 of the casing. To maintain integrity of the probe 14, a cover 20 is provided on the casing 12 which is movable to cover and uncover the probe 14.

Also on the front wall 18 of the casing 12, a reset switch 24 is provided. Alternatively, the meter 10 could be activated or deactivated upon opening and closing, respectively, of the cover 20, in known manner.

The embodiment of the meter 10 shown in FIG. 2 is substantially identical to that shown in FIG. 1, except for an engagement tab 28 by means of which the meter 10 can be engaged to a key chain or the like (not shown) and having a smaller size to the casing 12, for less bulk in a user's pocket.

Turning to FIG. 3, the simple circuit 30 for the meter 10 is illustrated. The circuit 30 is resident within the casing 12 and is seen to comprise a circuit 30 which functions by measuring resistance through the tobacco of a cigar 32. In this respect, the probe 14 is seated within an end 34 of the cigar 32 as shown in phantom and a reading is generated on the indicator 16. The indicator 16 may comprise a needle ammeter, an ohmmeter, a needle type indicator, a digital indicator 16 or any suitable form of indicator 16 for the circuit 30.

Further, indicator 16 could provide a number reading, or a word reading such as "wet", "dry", "good", etc, or a combination of the two.

The probe 14 is seen to comprise a ground sleeve electrode 36 surrounding a positive electrode 38, with the electrodes 36 and 38 being engaged to a power source 40 such as the 1.5 volt battery 40 depicted.

Interposed between the power source 40 and the electrodes 36 and 38 is a variable resistor 42 which calibrates the current through the indicator 16 upon activation of reset 24.

The differential across the electrodes 36 and 38 is used to indicate resistance which in turn indicates a corresponding calibrated moisture level in the tip 34 of the cigar 32 being tested, the resistance reading being amplified by a resistor/transistor coupling 44 prior to its being output to the indicator 16.

Use of the meter 10 will not only indicate smokability of the cigar 34 but will also indicate any adjustments which may be necessary to the user's humidor to provide enhanced smoking pleasure.

Turning now to FIGS. 4 and 5, it will be understood that a meter 10 incorporating various enhancements is not beyond the scope of the invention.

As shown, one or more enhancements may be incorporated into the meter 10. By way of example, and not to be construed as limiting to the scope of the invention, the meter 10 may also incorporate within the casing 12 thereof a lighter 46, or a cigar cutter 48, and further may incorporate a retractable probe 14, with the circuit 30 being activated by extension thereof and being deactivated by retraction thereof.

If desired, the casing 12 may be sectional, inasmuch as it is still preferred to maintain the casing small, with sections 50 and 52 of the casing being engaged through use of a hinge 54. therebetween, with the sections folding over each other to avoid becoming cumbersome to the user. Further, if desired, the circuit 30 may be activated and deactivated by relative positioning of the casing sections 50 and 52.

Thus a more versatile meter 10 is still shown to be within the scope of the invention.

As described above, the meter 10 provides a number of advantages, some of which are inherent in the invention and others of which become known upon perusal of the above description. Also, modifications may be proposed to the meter 10 without departing from the teachings herein. Accordingly, the scope of the invention is only to be limited as necessitated by the accompanying claims.

I claim:

1. A portable, handheld cigar moisture meter comprising a coverable or retractable probe having positive and ground leads of a resistance measuring circuit therein, the probe being injectable into a cigar tip by a cigar smoker for measuring differential across the leads correlating to a moisture content of the cigar which is indicated on an indicator.

2. The meter of claim 1 having a casing within which the circuit is house, with the probe extending outwardly of the casing.

3. The meter of claim 2 wherein the casing includes a probe cover.

4. The meter of claim 2 wherein the probe is retractable into the casing.

5. The meter of claim 1 having a reset.

6. The meter of claim 1 wherein the power source for the circuit is a battery.

7. The meter of claim 1 including a needle moisture indicator.

8. The meter of claim 1 including a digital display moisture indicator.

9. The meter of claim 2 wherein the casing includes an engagement tab for engaging the meter to a key chain.

10. The meter of claim 3 wherein the opening of the probe cover activates the circuit and closing of the probe cover deactivates the circuit.

11. The meter of claim 4 wherein extension of the probe activates the circuit and retraction of the probe deactivates the circuit.

12. The meter of claim 1 wherein a lighter is incorporated therein.

13. The meter of claim 1 wherein a cigar cutter is incorporated therein.

14. The meter of claim 2 wherein the casing comprises sections.

15. The meter of claim 14 wherein relative positioning of the sections activates and deactivates the circuit.

* * * * *